United States Patent [19]

Beck

[11] 4,262,521
[45] Apr. 21, 1981

[54] EPOXY RESIN GEL TESTER

[75] Inventor: Ronald A. Beck, Bloomington, Minn.

[73] Assignee: Sperry Corporation, New York, N.Y.

[21] Appl. No.: 70,181

[22] Filed: Aug. 27, 1979

[51] Int. Cl.³ .......................................... G01N 25/02
[52] U.S. Cl. ........................................ 73/17 R; 73/64.1
[58] Field of Search .................... 73/17 R, 15 R, 64.1

[56] References Cited

U.S. PATENT DOCUMENTS

| 3,020,748 | 2/1962 | Marshall et al. | 73/64.1 |
| 3,038,327 | 6/1962 | Resnick | 73/64.1 |
| 3,486,859 | 12/1969 | Greiner et al. | 73/64.1 X |
| 3,635,678 | 1/1972 | Seitz et al. | 73/64.1 X |
| 3,704,099 | 11/1972 | Sanz | 73/64.1 X |

*Primary Examiner*—Herbert Goldstein
*Attorney, Agent, or Firm*—Kenneth T. Grace; William E. Cleaver; Marshall M. Truex

[57] ABSTRACT

A method of and apparatus for determining the gel point of a sample of epoxy resin. An aluminum foil tube containing the sample is inserted into the test pressure sensor which is located within a preheated laboratory environmental chamber. The test pressure sensor consists of two knurled cylinders each rotatably mounted about its axis wherein the axes are parallel and the plane of the two axes is horizontal. The axis of one of the cylinders is fixedly mounted. The axis of the other cylinder is slidably mounted within the horizontal plane of the two axes. A spring tends to force the axis of the slidably mounted cylinder toward the axis of the fixedly mounted cylinder. The sample becomes liquid within the tube, and the two are drawn into the nip of the cylinders by their rotation. The cylinders continue to rotate collapsing the sample tube within the nip of the cylinders causing the liquid resin to be displaced above the nip of the cylinders within the sample tube. When the sample becomes a plastic wedge, signifying the gel point, it is drawn into the nip of the cylinders forcing them sufficiently apart to be measured by a set of electric contacts. A timer records the number of seconds between the insertion of the sample and the gel point.

8 Claims, 15 Drawing Figures

EPOXY RESIN GEL TESTER

BACKGROUND OF THE INVENTION

The present invention relates generally to techniques for testing physical properties of compositions of matter and more specifically to a technique for achieving repeatability in testing the gel point of an epoxy resin.

Many electronic component parts, such as printed circuit boards, use epoxy resins in their fabrication. Of great practical significance to processes using epoxy resins to fabricate these parts is the point at which a given epoxy resin becomes plastic, often known as gel point. It is common to measure the time required for a given epoxy resin to reach the gel point at a predetermined temperature. It can be shown that this gel point (time) for an epoxy resin changes from one production run to another and through storage conditions. Therefore, laboratory testing of each batch of epoxy resin is required prior to use in a further production step.

To date, the Fisher method of testing gel point time is the most popular. The method involves grinding the sample to be tested into a fine powder. The sample is placed on a metallic holder which has been heated to a predetermined temperature. The laboratory technician manually stirs the sample until he visually observes that the gel point has been reached. The technician also times the process manually with a stop watch. Because this manual process varies greatly from technician to technician, the results tend to vary greatly. A further problem is that since the test environment is essentially that of the laboratory, changes in ambient conditions greatly effect measured results.

SUMMARY OF THE INVENTION

The present invention uses the change in flow resistance of a sample of the gelling epoxy resin contained within a tube to force two feed rollers (i.e., knurled cylinders) apart, thus tripping a control switch. Because the feed rollers are under constant tension and rotate at a constant speed, much of the human error is sensing the gel point is eliminated, giving repeatable results. The use of an automatic clock greatly enhances the accuracy of elapsed time measurement. Since the entire test takes place within an environmental chamber, ambient variations within the laboratory have no affect upon the results.

The three involved calibratable variables involved are temperature, clock frequency and sensing threshold. The clock used has a 60 hertz oscillator which is calibratable using standard techniques. The sensing threshold is calibrated using shims of precise thickness inserted between the feed rollers to accurately determine when the electrical contacts of a test pressure sensor switch responsive to feed roller separation are mode and broken. This sensing calibration of feed roller separation is accomplishable within two one-thousandths of an inch. Temperatures is sensed through a platinum resistance unit and is regulated by a proportional control unit to an accuracy of ±0.2° F. from the desired set point.

DESCRIPTION OF THE PREFERRED EMBODIMENT

MECHANICAL

Figure 1:
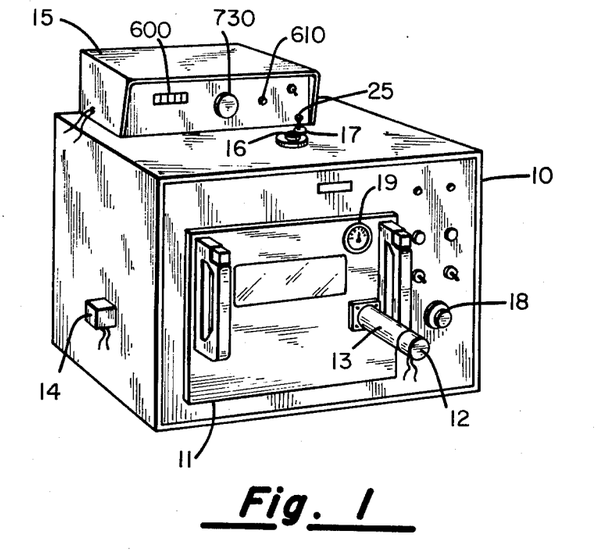
FIG. 1 shows the standard laboratory environmental chamber with modifications required to practice the present invention.

The preferred method of practicing the present invention uses a standard laboratory environmental chamber such as the Delta Design, Model 2300, labeled reference 10 in FIG. 1. It is expected that those of ordinary skill in the art could adapt other environmental chambers to practice the present invention. A constant temperature environment is desired for which 171° C. is currently in use.

The modifications to the laboratory environmental chamber as shown in FIG. 1 are the addition of sample entry orifice 16, sample entry orifice rotatable cover 17, sample entry preseat rod 25, test pressure sensor switch housing 14, test pressure sensor assembly motor 12, test pressure sensor assembly drive train 13, and timer and control circuit 15. Test pressure sensor assembly motor 12 and test pressure sensor assembly drive train 13 are mounted on removable front door 11. Timer and control circuit 15 is externally mounted on the top of laboratory environmental chamber 10. Temperature control 18 and thermometer 19 are used to control the temperature within the environmental chamber.

Figure 2:
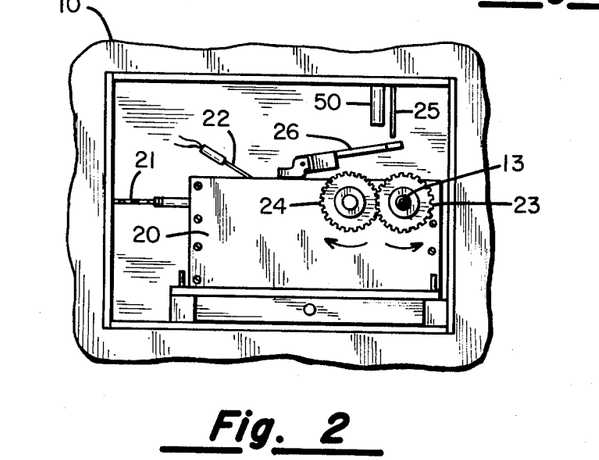
FIG. 2 is a front view of the test pressure sensor assembly.

FIG. 2 shows test pressure sensor assembly 20 which is mounted within laboratory environmental chamber 10 with removable front door 11 removed. Test pressure sensor shaft 21 is movable from left to right permitting activation of test pressure sensor switch 611 (shown in FIG. 8) which is located within test pressure sensor switch housing 14. See also FIG. 1. Thermocouple sensor probe 22 is used to ascertain that test pressure sensor assembly 20 is at the desired temperature (i.e., 171° C.). Fixed gear/shaft assembly 23 is driven by test pressure sensor assembly motor 12 (shown in FIG. 1) via test pressure sensor assembly train 13 in the direction shown. Movable gear/shaft assembly 24 is rotated in the direction shown because of the geared coupling with fixed gear/shaft assembly 23. Sample ejection rod 25 may be manually moved down engaging sample ejection lever 26. Sample 50 is dropped through sample entry orifice 16 into test pressure sensor assembly 20.

Figure 3:
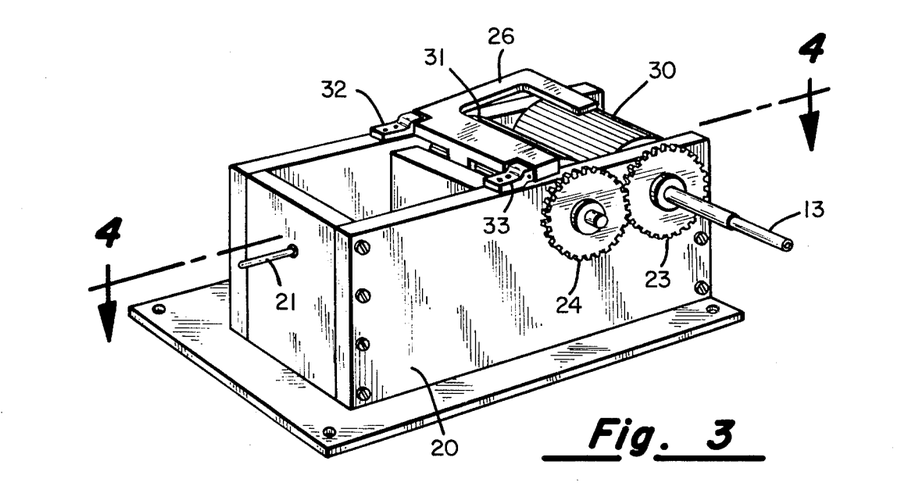
FIG. 3 is a prospective view of the test pressure sensor assembly.

FIG. 3 shows a prospective view of test pressure sensor assembly 20. Note that knurled cylinders 30 and 31 are fixedly coupled to fixed gear/shaft assembly 23 and movable gear/shaft assembly 24, respectively, causing knurled cylinders 30 and 31 to rotate in accordance, therewith. Sample ejection lever 26 is hingedly mounted to test pressure sensor assembly 20 by hinges 32 and 33.

Figure 4:
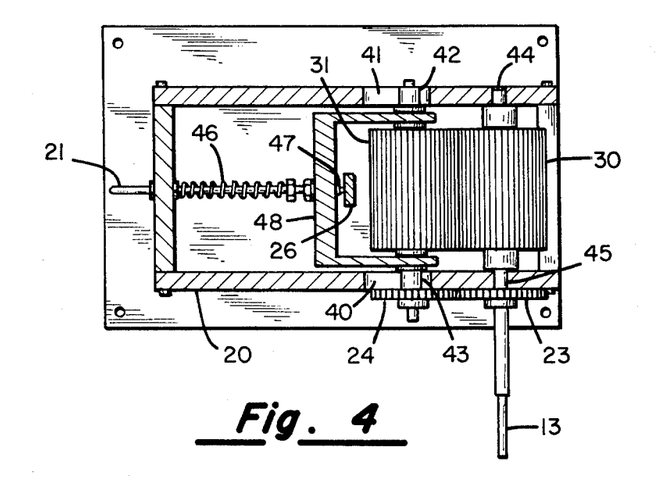
FIG. 4 is a top sectional view of the test pressure sensor assembly.

The sectional view in FIG. 4 shows the movable gear/shaft assembly 24, along with knurled cylinder 31 is free to slide within mounting slots 40 and 41 via bearings 42 and 43, whereas fixed gear/shaft assembly 23, along with knurled cylinder 30 is rotatably mounted to test pressure sensor assembly 20 via bearings 44 and 45. Some care should be exercised in choosing bearings 42, 43, 44, and 45 to ensure compatibility with the 171° C. resting temperature. Spring 46 tends to force test pressure sensor shaft 21 and carriage 48, and hence knurled cylinder 31, to the right. Test pressure sensor shaft 21 is fixedly mounted to carriage 48 via adjustment screw 47. Test shims may be inserted between knurled cylinder 31 and knurled cylinder 30 forcing carriage 48 and test pressure sensor shaft 21 to the left to determine the points at which the contacts of test pressure sensor switch 611 (shown in FIG. 8) open and close. Adjustment screw 47 is provided to regulate the incline of lever 26 to set its point of contact with sample ejection rod 25 and to thus control the amount of travel of carriage 48 and cylinder 31 when ejection rod 25 is depressed. Sample ejection rod 25 is normally held up by a spring (not shown).

The projection of sample ejection lever 26 is shown. As sample ejection rod 25 is manually pressed, it engages sample ejection lever 26. See FIG. 1 and FIG. 2. Sample ejection lever 26 is moved with respect to hinges 32 and 33 as seen in FIG. 3. As shown in FIG. 4, this causes carriage 48 and knurled cylinder 31 to move to the left permitting a previously tested sample 50 to drop free of knurled cylinder 31 and knurled cylinder 30 and thus be ejected from the test mechanism.

Figure 5:
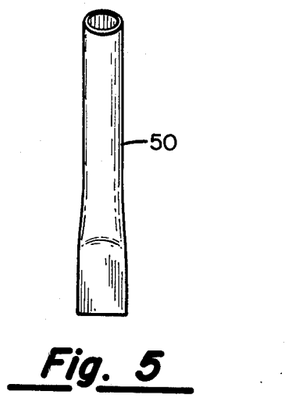
FIG. 5 is a view of the aluminum sample tube.

FIG. 5 shows a sample 50 as prepared for testing. A piece of aluminum foil of one one-thousands of an inch in thickness is rolled into a cylinder using a single thickness of the aluminum foil. The bottom end is pinched together as shown. A small amount of finely powdered epoxy resin is inserted into the top, partially filling the cylinder. The sample 50 is inserted into sample entry orifice 16 with the pinched end down. See also FIG. 2. The sample 50 frictionally lodges between knurled cylinder 30 and knurled cylinder 31 with the long axis of the pinch parallel to the axis of both knurled cylinder.

ELECTRICAL

Figure 6:
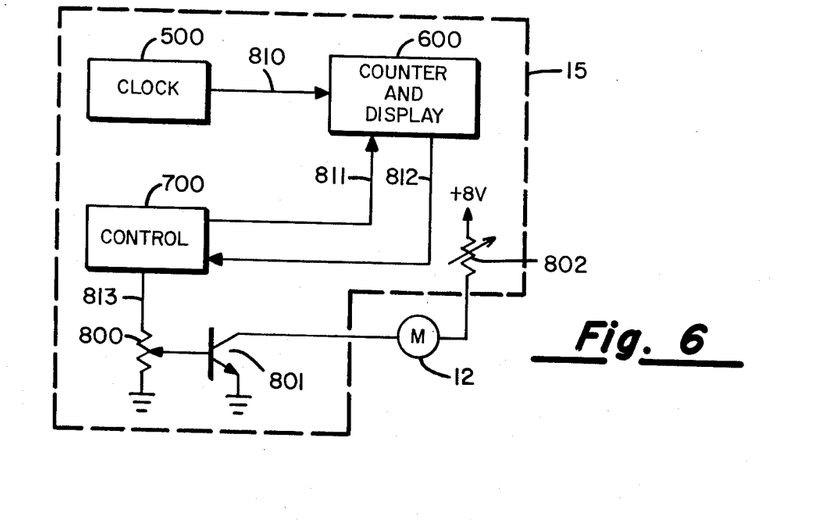
FIG. 6 is a block diagram of the timer and control circuitry.

FIG. 6 shows the overall timing and control circuitry in block diagram form. CLOCK 500 contains an oscillator and other circuitry to provide COUNTER AND DISPLAY 600 with a timing pulse once per second via line 810. COUNTER AND DISPLAY 600 counts the timing pulses and displays the count to the operator. Line 812 notifies CONTROL 700 of the position of the test pressure sensor switch 611 (shown in FIG. 8) contacts. COUNTER AND DISPLAY 600 receives a start counting signal from CONTROL 700 via line 811. COUNTER 700 drives test pressure sensor assembly motor 12 via line 813, potentiometer 800 and power transistor 801. Rheostat 802 determines the speed of test pressure sensor assembly motor 12. Potentiometer 800 is adjusted in accordance with power transistor 801 to cause test pressure sensor assembly motor 12 to be turned on and off in response to the control signal received from CONTROL 700 via line 813.

Figure 7:
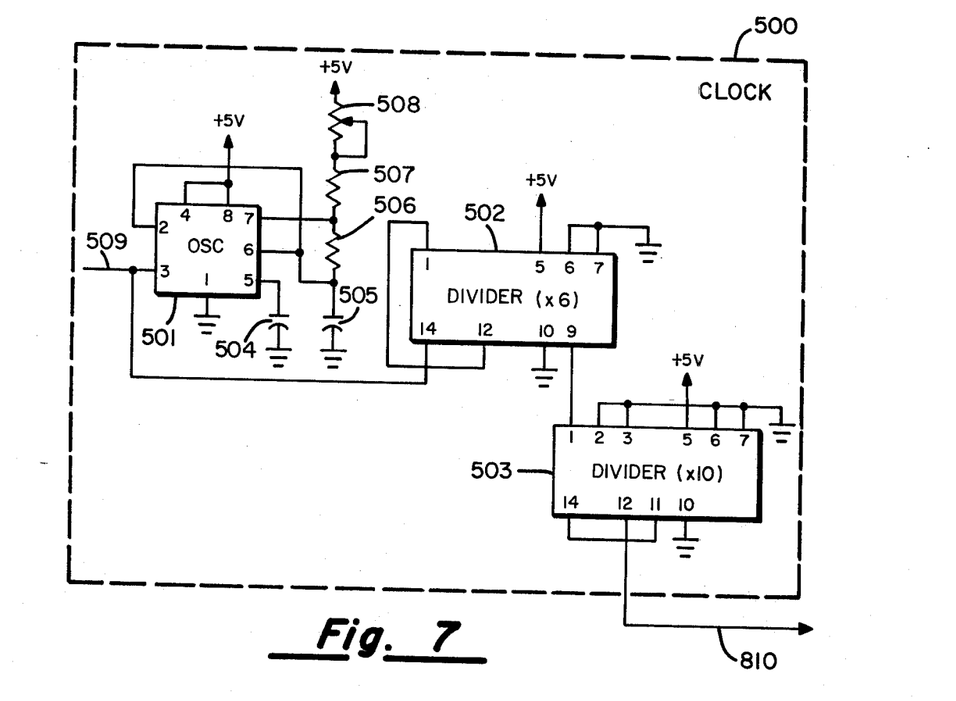
FIG. 7 is an electrical schematic drawing of the clock.
Figure 11:
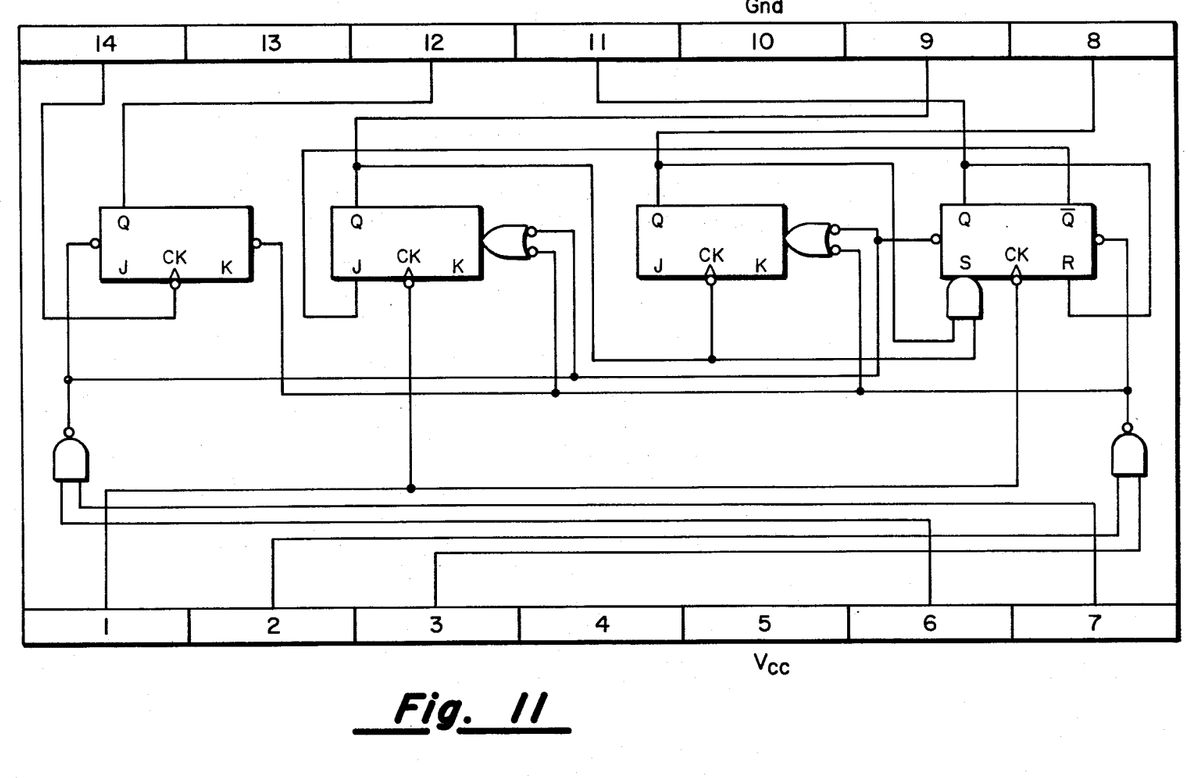
FIG. 11 shows the functional connections of the 7490 counter device.
Figure 12:
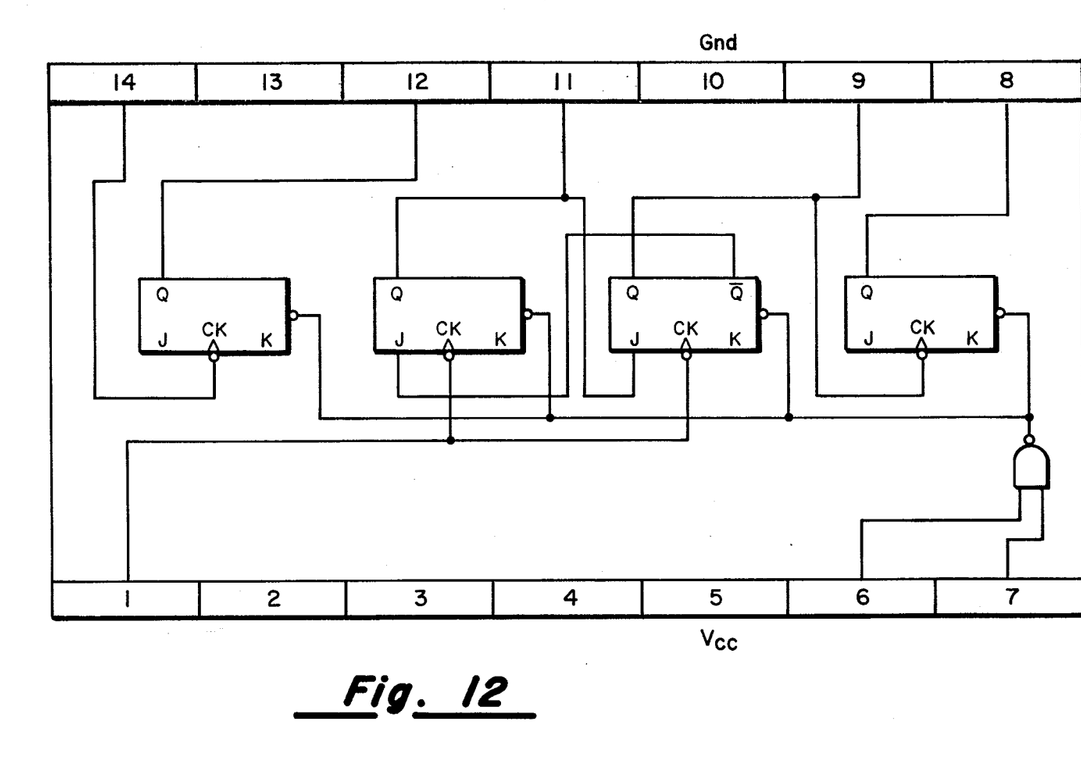
FIG. 12 shows the functional connections of the 7492 counter device.
Figure 14:
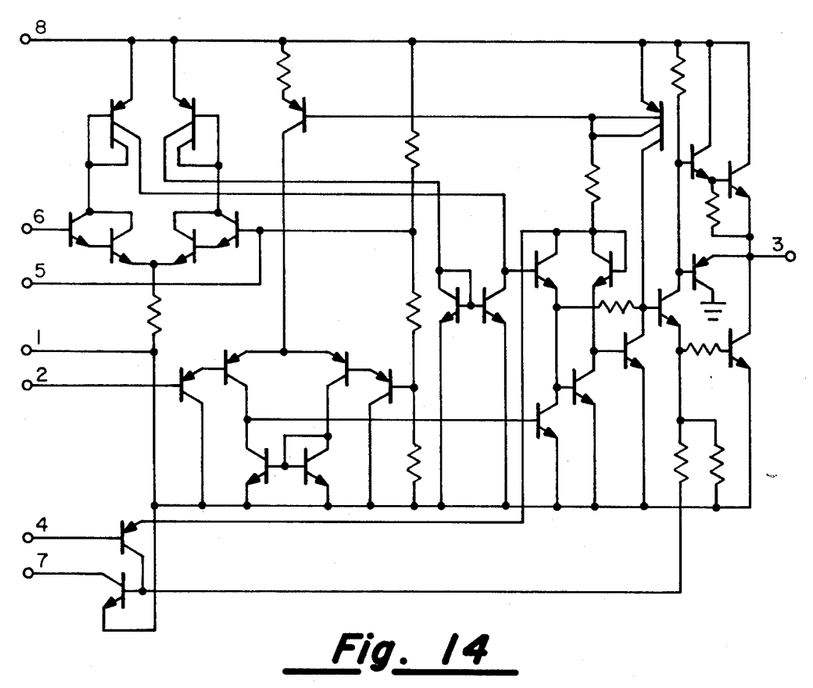
FIG. 14 shows the functional connections of the LM555 delay device.

FIG. 7 shows a detailed view of CLOCK 500. The oscillator 501 uses a National Semiconductor LM555 timer device. For the convenience of the reader, this circuit is shown in FIG. 14. Referring again to FIG. 7, capacitor 504 is 0.013 microfarads and capacitor 505 is 0.04 microfarads. Resistor 506 is 220,000 ohms and resistor 507 is 180,000 ohms. Variable resistor 508 is 50,000 ohms, which is adjusted to produce an output of 60 hertz when viewed with an oscilloscope at test point 509. DIVIDER (X6) 502 is a Texas Instruments, Incorporated, Ser. No. 7492. FIG. 12 provides the circuitry of the Ser. No. 7492. Referring again to FIG. 7, DIVIDER (X10) 503 is a Texas Instruments, Incorporated, Ser. No. 7490, a schematic of which is found in FIG. 11. The output of CLOCK 500, as shown in FIG. 7, is a one hertz signal transferred via line 810.

Figure 8:
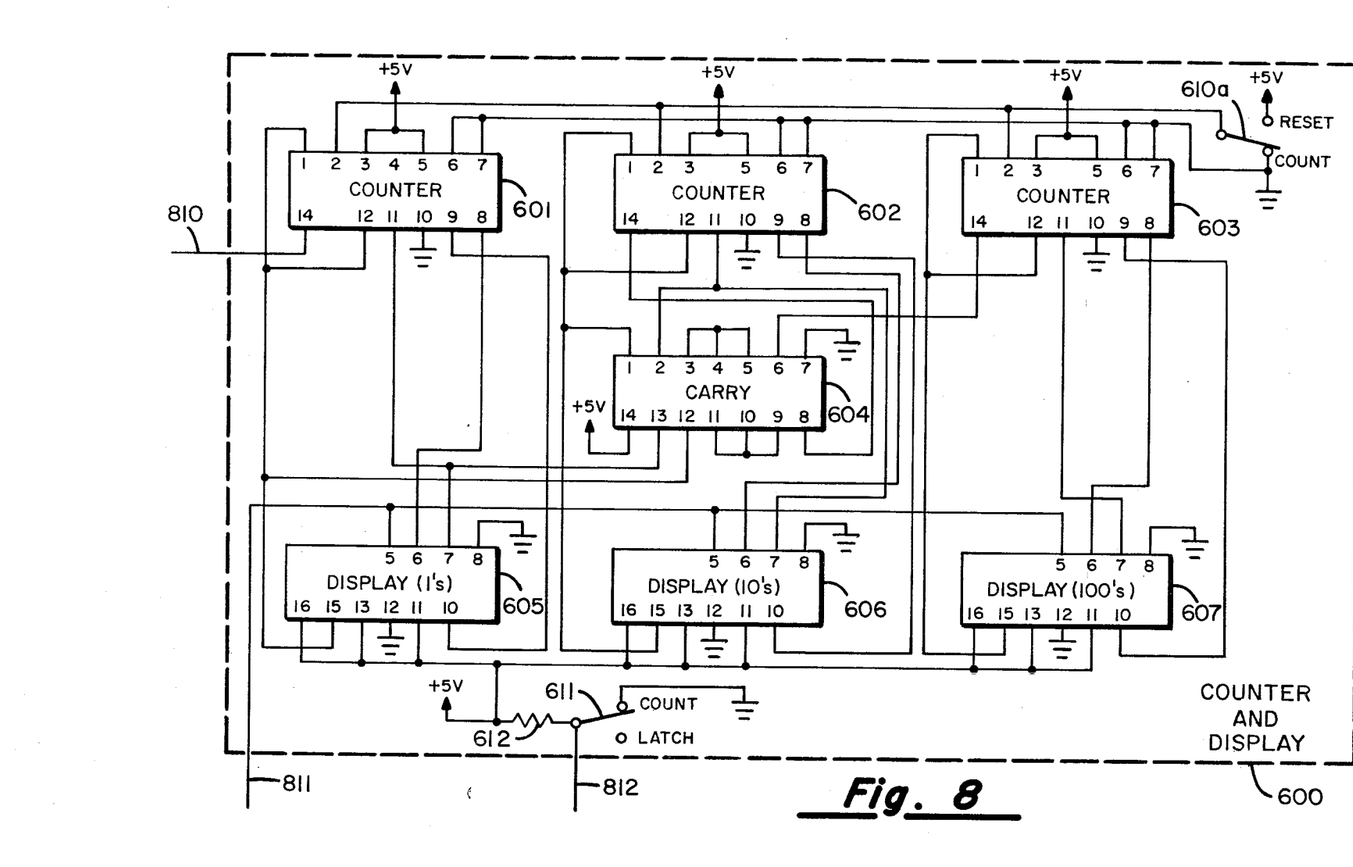
FIG. 8 is an electrical schematic drawing of the counter and display circuitry.
Figure 9:
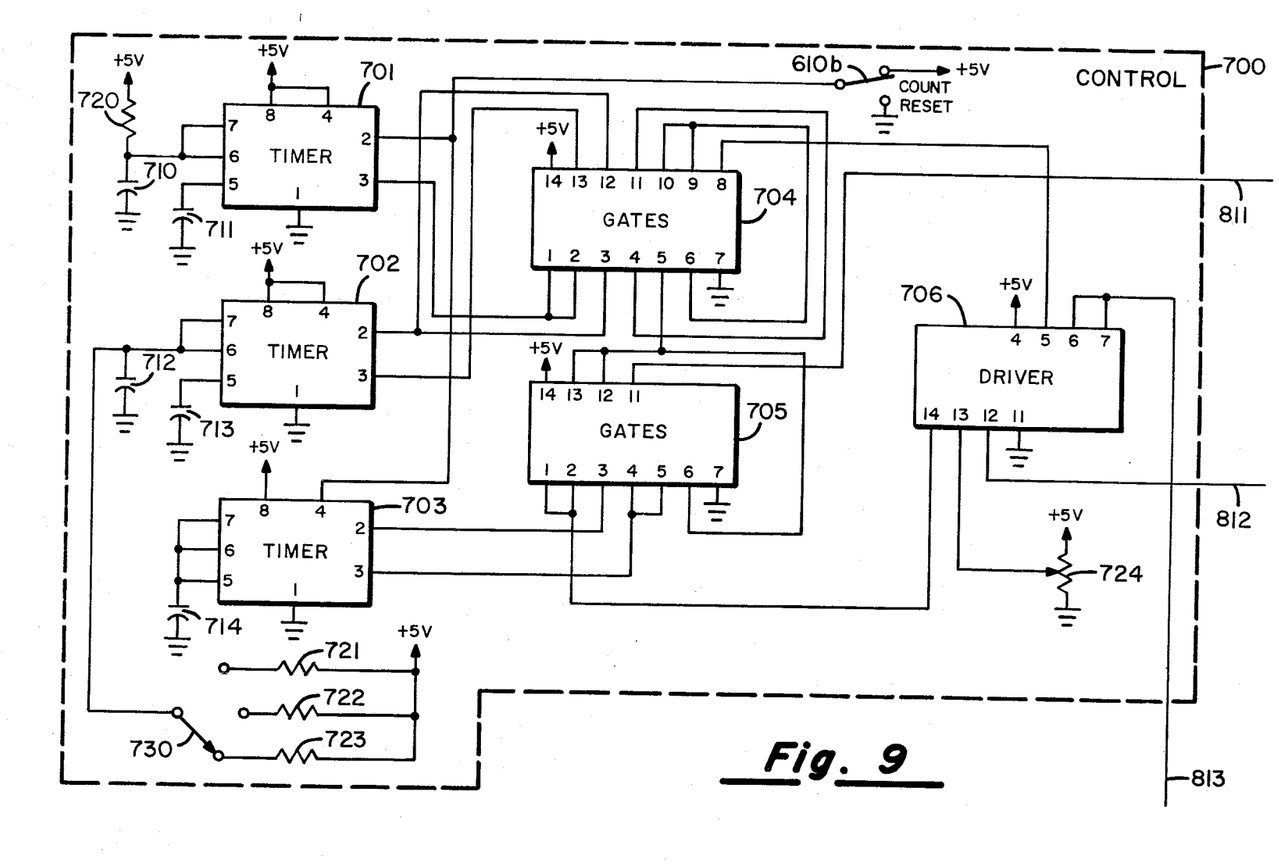
FIG. 9 is an electrical schematic drawing of the control circuit.
Figure 10:
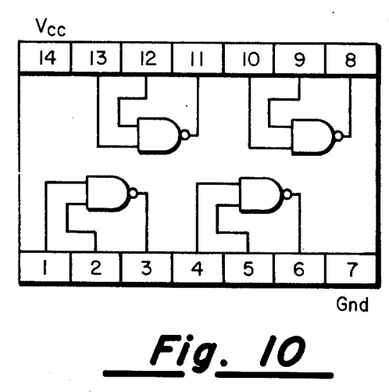
FIG. 10 shows the functional connections of the 7400-quad gate device.
Figure 15:
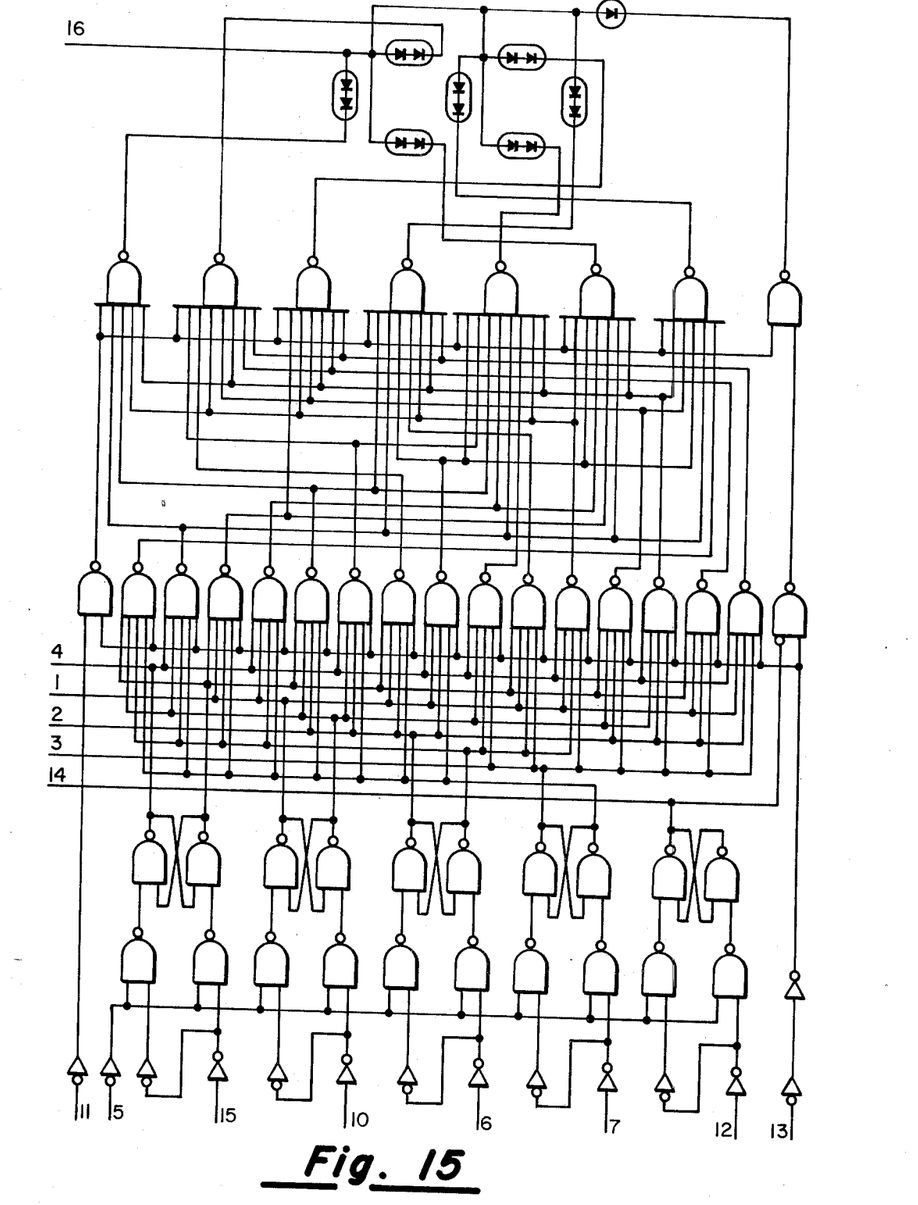
FIG. 15 shows the functional connections of the TIL 309 display device.

FIG. 8 shows the details of COUNTER AND DISPLAY 600. COUNTERs 601, 602, and 603 are implemented using Texas Instruments, Incorporated, Ser. No. 7490, a schematic of which is found in FIG. 11. CARRY 604 is a Texas Instruments, Incorporated, Ser. No. 7400, quad gate device, a schematic of which is found in FIG. 10. As seen in FIG. 8, DISPLAY (1's) 605, DISPLAY (10's) 606, and DISPLAY (100's) 607 are Texas Instruments, Incorporated TIL309, a schematic of which is found in FIG. 15. Referring again to FIG. 8, each counter (i.e., COUNTER 601, COUNTER 602, and COUNTER 603) counts one decade or power of ten. COUNTER 601 counts the one hertz signal received via line 810. COUNTER 602 counts tens of seconds. COUNTER 603 counts hundreds of seconds. The displays (i.e., DISPLAY (1's) 605, DISPLAY (10's) 606, and DISPLAY (100's) 607) display the contents of the corresponding counters. Switch 601a is one-half of a momentary contact push button switch 610, which half is normally in the count position. FIG. 9 contains the other half of the momentary contact push button switch (i.e., switch 610b). FIG. 8 shows test pressure sensor switch 611. The COUNT position results from test pressure sensor shaft 21 being moved to the left (see FIGS. 2, 3, and 4) and the LATCH position results from test pressure sensor shaft 21 being moved to the right. Referring again to FIG. 8, the COUNT position of Switch 611 grounds line 812 and through resistor 612, which is 3,900 ohms, enables the displays (i.e., DISPLAY (1's) 605, DISPLAY (10's) 606, and DISPLAY (100's) 607) to receive data rom the counters (i.e. COUNTER 601, COUNTER 602, and COUNTER 603.

Figure 13:
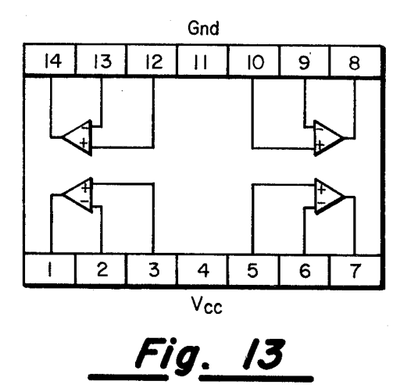
FIG. 13 shows the functional connections of the LM324-quad operational amplifier device.

CONTROL 700 is shown in detail in FIG. 9. TIMER 701, TIMER 702 and TIMER 703 are National Semiconductor LM555 devices, a schematic of which is found in FIG. 14. GATES 704 and GATES 705 are Texas Instruments, Incorporated, Ser. No. 7400 devices, a schematic of which is found in FIG. 11. DRIVER 706 is National Semiconductor LM324 quad operational amplifiers, a schematic of which is found in FIG. 13. Referring again to FIG. 9, capacitors 710, 711, 712, 713 and 714 are 8.0, 0.015, 10.0, 0.015, and 0.015 microfarads, respectively. Resistors 720, 721, 722, and 723 are 2.2, 11.0, 8.2, and 5.6 million ohms, respectively. Potentiometer 724 is 10,000 ohms. Switch 610b is one-half of a momentary contact push button switch 610 as previously discussed, which is normally in the COUNT position. Switch 730 is a single pole, three position switch which permits selection of one of three delay times as discussed below.

When sample 50 is inserted into sample entry orifice 16, switch 610 (i.e., 610a and 610b) is momentarily switched to the reset position. When switch 610 returns to the COUNT (i.e., normal) position, COUNTER AND DISPLAY 600 is enabled via line 811 and test pressure sensor assembly motor 12 is turned On via line 813 for a period of time determined by TIMER 703 and the setting of potentiometer 724 after which time test pressure sensor assembly motor 12 is turned off. The length of time test pressure sensor assembly motor 12 is permitted to be On is on the order of 20 seconds which enables the sample to be engaged by knurled cylinders 30 and 31. Test pressure sensor assembly motor 12 remains Off for a period of time and is then restarted at a time determined by TIMER 702 and switch 730. Resistor 721 provides about 120 seconds delay from the time of the release of switch 610. Resistor 722 provides about 90 seconds delay and resistor 723 provides about 60 seconds delay. This delay is desirable as it controls the amount of travel of sample 50 between knurled cylinders 30 and 31, permitting use of a smaller sample. Switch 730 permits selection of the delay, called "soak-time" to ensure that test pressure sensor assembly motor 12 has been restarted before the gel point is reached. After being restarted, test pressure sensor assembly motor 12 remains on until gel point is reached as notified via line 812.

OPERATION

The following steps are used to test a given sample:
(1) Momentarily depress sample ejection rod 25 to eject any previously tested sample from the test pressure sensor assembly 20. See FIGS. 1, 2, 3, and 4.
(2) Preheat laboratory environmental chamber 10 to 171° C. using temperature control 18 and thermometer 19. See FIG. 1.
(3) Calibrate as required (see below).
(4) Preselect "soak-time" with switch 730. See FIGS. 1 and 9.
(5) Prepare sample 50. See FIG. 5.
(6) Expose sample entry orifice 16 by rotating sample entry orifice rotatable cover 17. See FIG. 1.
(7) Insert sample 50 into sample entry orifice 16 with pinched-end down. See FIGS. 1 and 5.
(8) Momentarily depress switch 610 and notice that COUNTER AND DISPLAY 600 is reset to zero and begins counting. See FIGS. 1 and 8.
(9) Notice that test pressure sensor assembly motor runs for about 20 seconds as shown on COUNTER AND DISPLAY 600. See FIGS. 1 and 8.
(10) Notice that test pressure sensor assembly motor 12 restarts at a time determined by the "soak-time" setting of switch 730. See FIGS. 1 and 9.
(11) Notice that test pressure sensor assembly motor 12 stops and COUNTER AND DISPLAY 600 stops counting at the gel point and displays the elapsed time in seconds. See FIG. 1.

The value shown on COUNTER AND DISPLAY 600 is the measure (in seconds) of the gel point. If switch 730 is set to a soak-time that is too large, the resin may gel in the non-rotating cylinders at an indeterminate time. A soak-time setting on switch 730 that is too small may cause sample 50 to be driven beyond knurled cylinders 30 and 31 before the gel point is reached.

Sensing calibration is accomplished by adjusting a fine pitch screw (not shown) located in test pressure sensor switch housing 14 so that the spacing of test pressure sensor switch 611 contacts can be adjusted to actuate at exactly the thickness of the compressed aluminum foil tube, sample 50, plus a nominal thickness (0.005 inch ± 0.0010 inch) of gelled epoxy resin. Steel test shims placed between cylinders 30 and 31 while the apparatus is at temperature serve to simulate the desired thicknesses and limits and are used to dynamically set the actuation point of test pressure switch 611 and thus calibrate the sensing threshold.

What is claimed is:
1. Apparatus for measuring the gel point of a granular sample of epoxy resin, comprising:
   a sample tube of thin metal to hold said granular sample of epoxy resin;
   an environmental chamber capable of maintaining its interior at a predetermined temperature and having a sample entry orifice;
   a test pressure sensor assembly located within said environmental chamber, which test pressure sensor assembly receives said sample tube containing said granular sample of epoxy resin and applies over time a pressure thereto that will cause a lesser or greater deformation of said sample tube dependent upon whether said epoxy resin contained therein is in a granular state or is in a plastic state, and which senses that said granular sample of epoxy resin has entered a plastic state;
   a first switch for indicating that said sample tube containing said granular sample of epoxy resin has been inserted into said sample entry orifice; and
   a controller responsively coupled to said test pressure sensor assembly and said first switch for determining the length of time that elapses between when said first switch indicates that said sample tube containing said granular sample of epoxy resin has been inserted into said sample entry orifice and when said test pressure sensor assembly senses that said granular sample of epoxy resin has entered said plastic state whereby said length of time is a measure of the gel point of said granular sample of epoxy resin.
2. Apparatus according to claim 1 wherein said test pressure sensor assembly further comprises:
   a base;
   a first roller mounted to said base;
   a second roller slidably mounted to said base;
   a spring coupled to said second roller and said base tending to force said second roller towards said first roller; and
   a second switch coupled to said second roller and said controller whereby said second switch indicates to said controller when a non-plastic sample is positioned between said first roller and said second roller.
3. Apparatus according to claim 2 wherein said first roller and said second roller are mounted to said base having parallel axes.
4. Apparatus according to claim 3 wherein said first roller and said second roller are rotatably mounted to said base.
5. Apparatus according to claim 4 further comprising:
   a motor coupled to said first roller, said second roller, and said controller whereby said motor causes said first roller and said second roller to rotate in such a fashion as to pinch said sample tube whenever said first switch indicates to said controller that said sample tube has been inserted into said sample entry orifice and whereby said motor causes said first roller and said second roller to not rotate whenever said second switch indicates to said controller that said non-plastic sample is not positioned between said first roller and said second roller.

6. A method of measuring the gel point of a sample of epoxy resin comprising:

preheating an environmental chamber to a predetermined temperature;

preparing said sample of epoxy resin by grinding it into a fine powder and placing said fine powder into a thin metal tube;

inserting said prepared sample of epoxy resin into said preheated environmental chamber;

lodging said sample of epoxy resin between slidable coupled rollers;

measuring the force whereby said slidably coupled rollers are separated by said lodging;

measuring the change of force whereby said slidably coupled rollers are separated as said sample of epoxy resin reaches said plastic state; and, measuring the time required between the lodging of said sample of epoxy resin between said slidably coupled rollers and when the change of force between said slidably coupled rollers indicates that said epoxy resin has reached said plastic state.

7. Apparatus for measuring the gel point of an epoxy resin, comprising:

sample means for containing a non-plastic sample of an epoxy resin;

means for maintaining said sample means at a temperature that is sufficient to change said sample of epoxy resin from a non-plastic state to a plastic state;

test pressure sensor assembly means for receiving and compressing said sample means, which test pressure sensor assembly means senses the pressure applied to said sample means for determining when said non-plastic sample of epoxy resin has entered a plastic state;

first switch means for indicating that said test pressure sensor assembly means has received said sample means; and controller means responsively coupled to said test pressure sensor assembly means and said first switch means for determining the length of time that elapses between when said first switch means indicates that said test pressure sensor assembly means has received said sample means and when said test pressure sensor assembly means senses that said non-plastic sample of epoxy resin has entered said plastic state whereby said length of time is a measure of the gel point of said epoxy resin.

8. Apparatus according to claim 7 wherein said test pressure sensor assembly means further comprises:

first and second roller means compressively coupled for receiving and springly compressing said sample means therebetween; and, second switch means coupled to said second roller means and said controller means whereby said second switch means indicates to said controller means when a non-plastic sample of said epoxy resin is positioned between said first roller means and said second roller means.

* * * * *